United States Patent [19]

Kotake et al.

[11] Patent Number: 5,581,460
[45] Date of Patent: Dec. 3, 1996

[54] MEDICAL DIAGNOSTIC REPORT FORMING APPARATUS CAPABLE OF ATTACHING IMAGE DATA ON REPORT

[75] Inventors: Takashi Kotake; Sayuri Matsumoto, both of Tokyo, Japan

[73] Assignee: Kabushiki Kaisha Toshiba, Tokyo, Japan

[21] Appl. No.: 205,772

[22] Filed: Mar. 4, 1994

Related U.S. Application Data

[63] Continuation of Ser. No. 788,418, Nov. 6, 1991, abandoned.

[30] Foreign Application Priority Data

Nov. 6, 1990 [JP] Japan .................................. 2-298882
Dec. 13, 1990 [JP] Japan .................................. 2-402045

[51] Int. Cl.⁶ .......................................................... G06F 17/60
[52] U.S. Cl. ........................................ 395/203; 364/413.01
[58] Field of Search .......................... 364/413.01, 413.02, 364/413.13, 401; 395/147, 135, 149, 158, 165, 400

[56] References Cited

U.S. PATENT DOCUMENTS

| | | | |
|---|---|---|---|
| 4,817,050 | 3/1989 | Komatso et al. | 364/900 |
| 4,847,694 | 7/1989 | Nishihara | 358/434 |
| 4,945,476 | 7/1990 | Bodick et al. | 364/413.02 |
| 4,958,283 | 9/1990 | Tawara et al. | 364/413.13 |
| 5,019,975 | 5/1991 | Mokai | 364/413.03 |
| 5,086,392 | 2/1992 | Nakajima | 364/413.22 |
| 5,140,518 | 8/1992 | Ema | 364/413.01 |
| 5,148,366 | 9/1992 | Buchanan et al. | 364/419 |

Primary Examiner—Gail O. Hayes
Assistant Examiner—Hayward Verdun
Attorney, Agent, or Firm—Oblon, Spivak, McClelland, Maier, & Neustadt, P.C.

[57] ABSTRACT

To automatically form a medical diagnostic report containing various patient's information and also relevant medical diagnostic image data, a plurality of medical diagnostic image data are previously registered. The medical diagnostic report forming apparatus includes an image data registering portion for previously registering therein a plurality of medical diagnostic image data on patients. An extracting portion is also provided for extracting desirable medical diagnostic image data from plural image data registered in the image data registering portion to obtain the desirable diagnostic image data. A keyboard is also provided for entering doctor's comment data related to the desirable diagnostic image data; with a main memory having a report forming memory region for writing the desirable diagnostic image data together with the doctor's comment data. As a result, a medical diagnostic report containing at least both of the desirable diagnostic image data and the doctor's comment data is formed.

13 Claims, 11 Drawing Sheets

MEDICAL DIAGNOSTIC REPORT FORMING APPARATUS CAPABLE OF ATTACHING IMAGE DATA ON REPORT

This application is a Continuation of application Ser. No. 07/788,418, filed on Nov. 6, 1991, now abandoned.

BACKGROUND OF THE INVENTION

1. Field of the Invention

The present invention generally relates to a medical diagnostic report forming apparatus. More specifically, the present invention is directed to such a report forming apparatus capable of easily attaching medical diagnostic image data on the medical diagnostic report with doctor's comments.

2. Description of the Prior Art

In general hospital report supervising systems, when a radiological doctor diagnoses medical examination images acquired by X-ray apparatuses or the like, he forms medical diagnostic reports based upon his diagnostic judgements, and then furnishes these diagnostic reports to departments which request such diagnosis and simultaneously stores them, which will be available during subsequent medical examinations. A typical medical diagnostic report is mainly constructed of four information columns and relevant image data. That is, they are a patient information column on which a name of a patient and a birthday of the patient are described; an examination information column on which an examination date and a name of examining department are described; a clinical information column on which clinical information of the patient is described; and a doctor's comment data column on which doctor's comments are described. The relevant image data required for explaining his diagnostic judgements is attached to the fourth information column (i.e., doctor's comment column) with a free space. This implies that any of report forming persons, e.g., doctors must input medical image data of patients into such doctor's comment data column every time the diagnostic report is formed, which necessarily requires cumbersome operations as well as heavy workloads.

Furthermore, since each of the image data is contained in each of such medical diagnostic reports, a memory having a large memory capacity is necessarily required so as to store these medical diagnostic reports.

On the other hand, in another conventional medical report forming apparatus, a plurality of image data on various patients have previously been registered in this report forming apparatus in order to avoid such heavy workloads given to doctors that the image data are acquired by utilizing the image scanner and film digitizers every time the doctors form the medical diagnostic reports.

In general, 8 different sorts of images are registered in a single memory page, which can be displayed on the monitor at the same time. Then, a doctor seeks a desirable image from a first memory page containing 8 different images. If there is no desirable image in the first memory page, then he must screen a second memory page containing 8 sheets of medical images different from those of the first memory page. If the desirable image is not available from the second memory page, then he must continue his search operation for the subsequent memory pages. However, the order of 8 different sheets of medical images contained in the respective memory pages is always the same, and furthermore the images contained in the memory pages are always and successively displayed in the order from the first memory page to the last memory page, irrelevant to their frequencies of use. This implies that the cumbersome and useless image-searching operations must be repeated until the desirable image is available.

SUMMARY OF THE INVENTION

The present invention has been made in an attempt to solve the above-described drawbacks, and therefore has an object to provide a medical diagnostic report forming apparatus capable of attaching a desirable medical image to a medical diagnostic report with very easy operation.

A further object of the present invention is to provide a medical diagnostic report forming apparatus capable of storing a plurality of medical diagnostic reports into a storage device having a small memory capacity, although the respective medical diagnostic reports contain the desirable image data which require or occupy a large memory region of the storage device.

A still further object of the present invention is to provide a medical diagnostic report forming apparatus capable of displaying medical images in the order of their frequencies of use. In a particular embodiment, one medical image which has been used as the desirable image during the last report forming operation, is displayed at top priority during the present report forming operation, prior to displaying of other registered images.

To achieve the above-described objects and other features of the present invention, a medical diagnostic report forming apparatus comprises:

image data registering means for previously registering therein a plurality of medical diagnostic image data on patients;

means for extracting desirable medical diagnostic image data from said plural image data registered in said image data registering means to obtain the desirable diagnostic image data;

means for entering doctor's comment data related to said desirable diagnostic image data; and, main memory means having a report forming memory region for writing therein said desirable diagnostic image data together with said doctor's comment data, whereby a medical diagnostic report containing at least both said desirable diagnostic image data and said doctor's comment data is formed.

Furthermore, a medical diagnostic report forming apparatus comprises:

image data registering means for previously registering therein a plurality of medical diagnostic image data on patients with attaching registration numbers thereto, said registration numbers indicating said corresponding medical diagnostic image data;

means for extracting desirable medical diagnostic image data with a preselected registration number from said plural image data registered in said image data registering means to obtain the desirable diagnostic image data;

means for entering doctor's comment data related to said desirable diagnostic image data;

main memory means having a report forming memory region for writing therein said desirable diagnostic image data together with said doctor's comment data, whereby a medical diagnostic report containing at least both said desirable diagnostic image data and said doctor's comment data is formed; and, means for rearranging said registration numbers of said plural diagnostic image data in such a manner that said desirable diagnostic image data has top priority to be extracted by said image data extracting means during a subsequent report forming operation.

BRIEF DESCRIPTION OF THE DRAWINGS

For a better understanding of the present invention, reference is made of the following detailed description of the present invention to be read in conjunction with the following drawings, in which.

DETAILED DESCRIPTION OF THE PREFERRED EMBODIMENTS

Overalll Arrangement of First Medical Diagnostic Report Forming Apparatus

Figure 1:
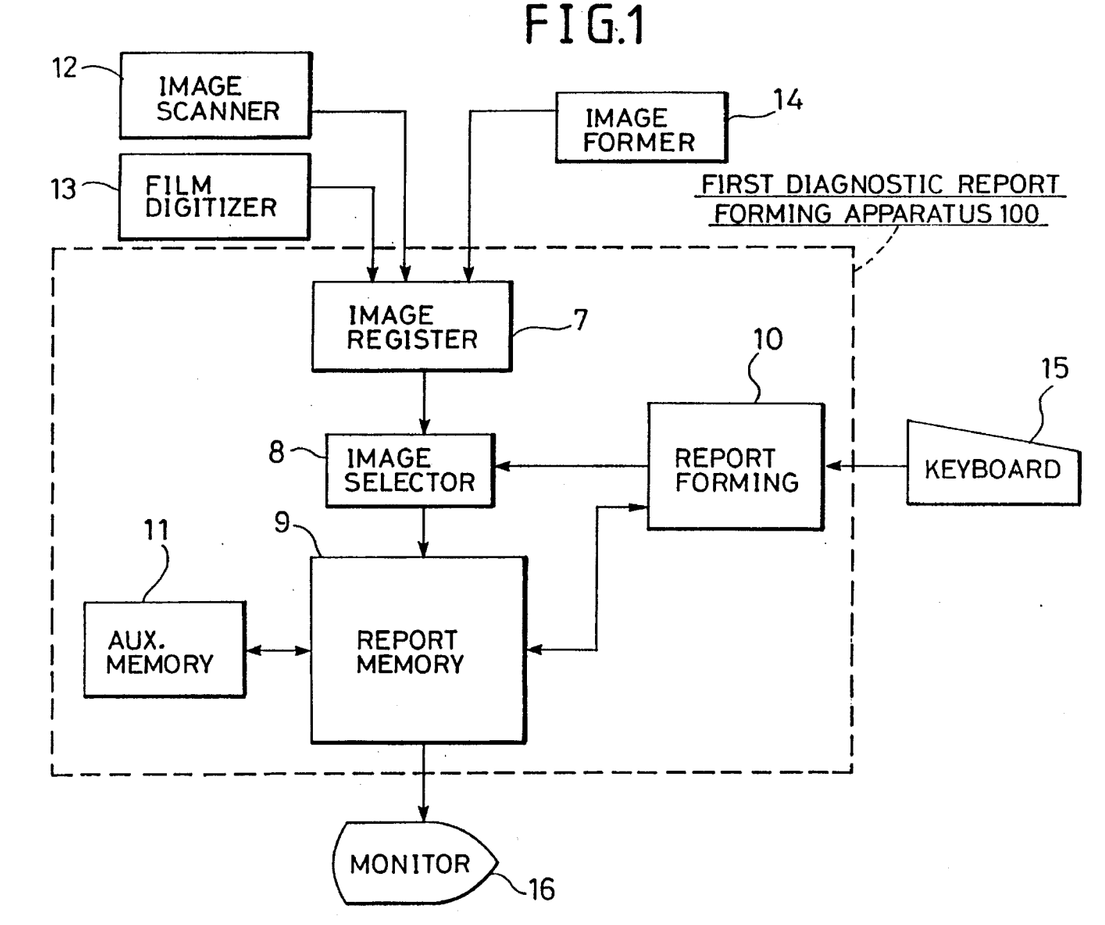
FIG. 1 is a schematic block diagram for showing an overall arrangement of a medical diagnostic report forming apparatus according to a first preferred embodiment of the present invention.

In FIG. 1, there is shown an overall arrangement of a medical diagnostic report forming apparatus 100 according to a first preferred embodiment of the present invention.

The first medical diagnostic report forming apparatus 100 is mainly constructed of an image data registering unit 7, an image data selecting unit 8, a medical diagnostic report forming memory 9, a medical diagnostic report forming unit 10, and an auxiliary memory 11.

The image data registering unit 7 previously registers various medical image data which are supplied from an image scanner 12, a film digitizer 13, and an image forming means 14. The image forming means 14 forms medical images by utilizing a mouse and a pointing device (not shown in detail).

The image data selecting unit 8 extracts desired image data from the above-described image data registered from the registering unit 7 so as to output the desired image data to the diagnostic report forming memory 9 in response to an instruction issued from the medical report forming unit 10.

The medical diagnostic report forming memory 9 has a memory space, or region for forming a diagnostic report 20 (see FIG. 2) therein, and forms the medical diagnostic report 20 in such a manner that the desirable image data selected from the image data selecting unit 8 is attached thereto and also doctor's comment information is written therein.

Figure 2:
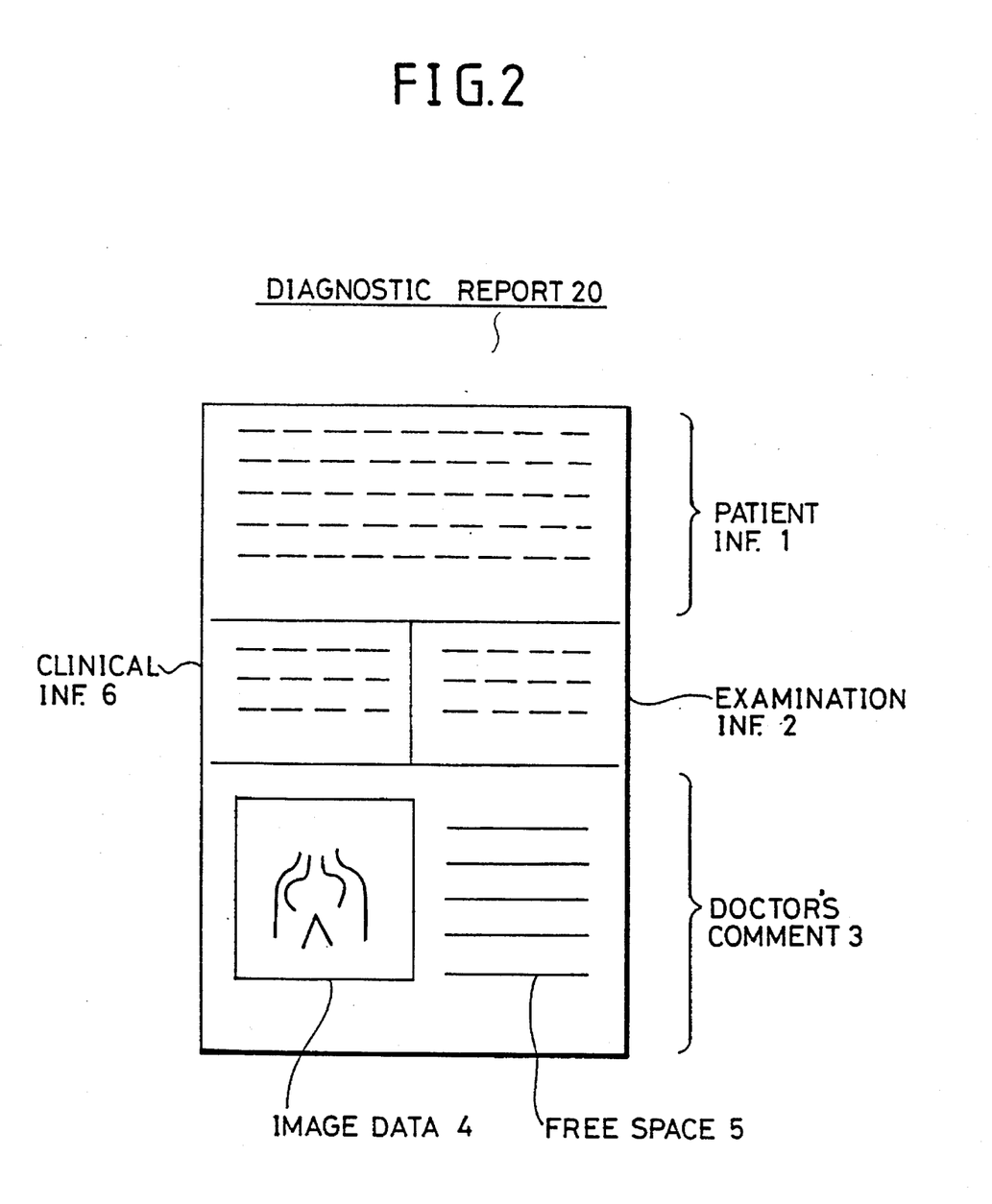
FIG. 2 schematically illustrates a medical diagnostic report 20 formed by the first medical diagnostic report forming apparatus 100 according to the present invention.

Here, one medical diagnostic report 20 is illustrated in FIG. 2. This medical diagnostic report 20 is constructed of a patient information (for instance, an identification number, a patient name, a patient birth date, and sex) column 1; an examination information (an examination day, a diagnostic department, and a medical sheet) column 2; a doctor's comment column 3; image data 4 of the patient; a free space 5 for remarks, and a clinical information (comment by clinic staff) column 6.

Referring back to FIG. 1, the medical report forming unit 10 supplies the above-described image data selecting instruction to the selecting unit 8 by acquiring both an image selecting signal and various doctor's comment data inputted from the keyboard 15, and also writes the various doctor's comment data into the image report forming memory 9. It should be noted that the various doctor's comment data includes the above-described patient information 1, examination information 2, doctor's comment 3, and clinical information 6 as shown in FIG. 2.

The auxiliary memory 11 stores therein the medical diagnostic report 20 formed in the report forming memory 9.

The medical diagnostic report 20 is also outputted to a monitor 16 for monitoring purposes.

A keyboard 15 is connected to the medical report forming unit 10 in order to enter the image selecting signal and the various doctor's comment data.

As previously explained, to issue the image selecting signal from the keyboard 15, an operator makes a decision via the keyboard 15 while observing the various medical images previously registered in the image data registering unit 7 and displayed on the monitor 16.

MEDICAL REPORT FORMING OPERATION

A medical report forming operation by the above-described first medical report forming apparatus 100 will now be summarized with reference to FIGS. 1 and 2.

As previously stated, the image data on patients which are selected and attached on the respective medical diagnostic reports 20, have been previously registered into the image data registering unit 7 by means of the image scanner 12, film digitizer 13 and image forming means 14. As utilized herein, the reference to "previously registered" image data refers to data which has been previously entered and stored, with image data other than the patient's own image data. Thus, the report can be formed without requiring image data to be entered for each patient in order to form a report which includes images. The images are initially entered by the image scanner 12, film digitizer 13 and image forming means 14, and the initial entry of such images may be provided by the users (i.e., the doctor or his staff) of the report forming apparatus, or by a third party such that the doctor or his staff need not originally enter the image data.

When an operator inputs the image selecting signal and the various doctor's comment data via the keyboard 15 to the report forming unit 10, while observing the various medical images on the monitor 16, these selecting signal and various doctor's comment data are acquired by the medical report forming unit 10.

In response to the image selecting signal, the image data selecting unit 8 selects the desirable medical image data. Then, the desirable medical image data is written into the report forming memory 9. On the other hand, the various doctor's comment data such as the patient information, examination information and clinical information are written into the relevant memory locations (i.e., the patient information column 1, examination information column 2 and clinical information column 6 as shown in FIG. 2) of the report forming memory 9.

Thereafter, thus formed medical diagnostic report 20 is stored in the auxiliary memory 11. At this time, the image data 4 attached to this medical diagnostic report 20 is stored in this memory 11 as a form of a preselected registration number of the registering unit 7, instead of this image data 4 itself. It should be noted that when all of the image data acquired by, for instance, the image scanner 12 and film digitizer 13 are registered in the image data registering unit 7, the registration numbers are determined in a serial mode by way of an interactive system (will be discussed later) and the keyboard 15 with the monitor 16. In other words, a preselected registration number corresponding to the selected image data attached to the diagnostic report 20 is stored in this auxiliary memory 11. Accordingly, when the diagnostic report data is read out from the auxiliary memory 11, since the preselected registration number corresponding to the selected image data attached to this diagnostic report data is merely derived therefrom, this selected image data is retrieved from these image data registered in the registering unit 7 based on this registration number. Subsequently, the retrieved image data is supplied to the report forming memory 9 in which this retrieved image data is electrically attached or combined with the diagnostic data read out from the auxiliary memory 11, whereby the medical report 20 can be formed.

As previously described in detail, in accordance with the first medical diagnostic report forming apparatus 100, the image data which are to be utilized when the medical diagnostic reports are formed, have been previously registered in the image data registering unit 7. Then, a selection is made of the desirable image data from the image data registered in the image data register unit 7, and the selected image data is attached to the relevant diagnostic report 20, whereby the desirable medical diagnostic report 20 can be formed. As a consequence, since an operator no longer inputs the image data every time the diagnostic report is formed, workloads given to the operator can be considerably reduced.

In addition to the above-explained particular advantage, these is another merit of this first preferred embodiment.

That is, since the selected image data written on the diagnostic report data is stored in the form of registration number in the auxiliary memory 11, a total data amount of the diagnostic report can be reduced and therefore any auxiliary memory each having a small memory capacity can sufficiently store such report data.

INTERNAL ARRANGEMENT OF FIRST DIAGNOSTIC REPORT FORMING APPARATUS

Figure 3:
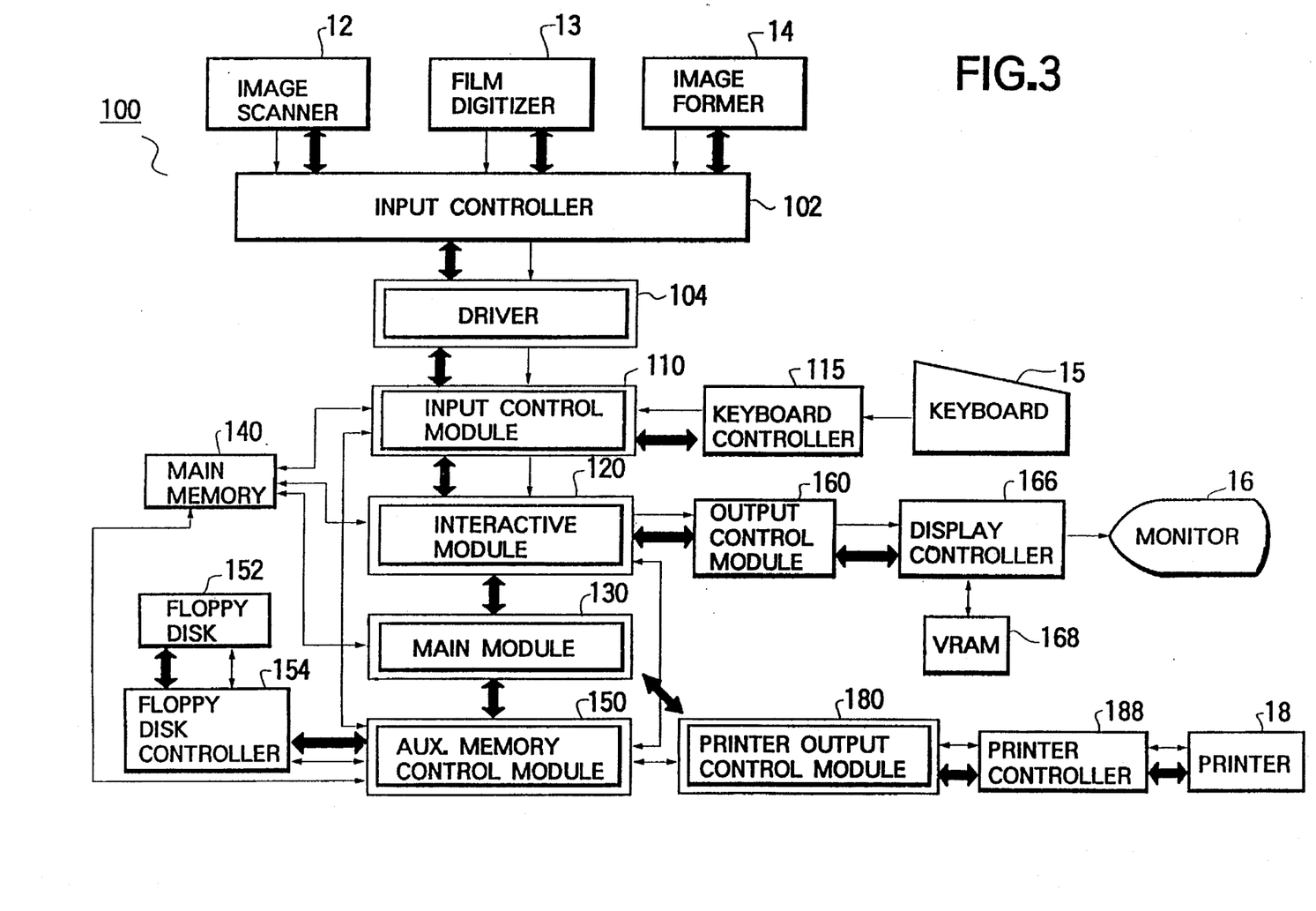
FIG. 3 is a schematic diagram for showing an internal arrangement of the first medical diagnostic report forming apparatus 100 shown in FIG. 1.

FIG. 3 is a schematic block diagram for showing an internal arrangement of the first diagnostic report forming apparatus 100 shown in FIG. 1.

This internal arrangement is mainly constructed of: an input controller 102; an input control module 110; an interactive module 120; a main module 130; a main memory 140 (corresponding to the medical report forming memory 9 of FIG. 1); and an auxiliary memory control module 150, and also an output control module 160. In this figure, a printer 18 is additionally employed.

The input controller 102 is of RS-232C regulation type input controller, and is communicated to the image scanner 12, film digitizer 13 and image former 14 such as a mouse (not shown in detail). The image data acquired under control of the input controller 102 are transferred via a driver 104 to the input control module 110. To this input control module, the keyboard 15 is connected via a keyboard controller 115. The image data are further transferred to the interactive module 120 and then to the auxiliary memory control module 150.

To this interactive module 120. the monitor 16 is connected via a display controller 166 and the output control module 160. A VRAM 168 is connected to the display controller 160. Also, to the auxiliary memory control module 150, a floppy disk apparatus 152 (corresponding to the auxiliary memory 11 of FIG. 1) is connected via a floppy disk controller 154, and the printer 18 is connected via a printer controller 188 and a printer output control module 180.

The main module 130 is communicated with the main memory 140, the printer output control module 180, the interactive module 120 and auxiliary memory control module 150.

DETAILED OPERATION OF FIRST MEDICAL DIAGNOSTIC REPORT FORMING APPARATUS

Referring now to a flow chart shown in FIG. 4, the medical report forming operation by the first medical diagnostic report forming apparatus 100 will be described more in detail.

At a first step ST-10 of this flow chart, the patient ID (identification) number is read out from a diagnostic request card and then inputted via the keyboard 15 into the first medical report forming apparatus 100 by a doctor. At a next step ST-12, a check is made whether or not there is a past medical record of this patient. If YES, then the patient information 1 as shown in FIG. 2 is displayed on the monitor 16 at a step ST-14. To the contrary, if NO, then an indication "NO PATIENT RECORD" is made at a step ST-16. Thereafter, patient information is newly entered by the keyboard 15 into the medical diagnostic report 20 at a step ST-18.

Then, at a step ST-20, the examination information 2 as shown in FIG. 2 is similarly entered into the report 20 via the keyboard 15 by the doctor. Furthermore, clinical information 6 as shown in FIG. 2 is inputted into the report 20 via the keyboard 15 at the next step ST-22. As a result, an image menue is displayed on the monitor 16 via the output control module 160 and display controller 166 at a step ST-24.

At a subsequent step ST-26, the desirable image data is selected (e.g., from previously registered image data other than the patient's own image data, which has been previously registered in the image data registering unit) in the interactive mode under control of the interactive module 120. Then, the operator manipulates the mouse 14 to point out the position to be considered at a step 28, so that a line and a registration number are automatically attached to the selected image data of this report 20 at a step 30.

Next, the doctor inputs his comment 3 as shown in FIG. 2 via the keyboard 15 into the report 20 at a step-32, and also inputs a diagnostic code via the keyboard 15 into the report 20 at a step-34. Furthermore, doctor information such as doctor's name, and a name of diagnostic department is entered via the keyboard 15 into the free space 5 of the report 20 at a step ST-36.

At a next step 38, the resultant medical diagnostic report 20 is printed out by the printer 18 under control of the printer output control module 180 and the printer controller 188. Moreover, this resultant medical diagnostic report 20 is stored in the floppy disk apparatus 152 under control of the auxiliary memory control module 150 and the floppy disk controller 154 at a final step ST-40.

As easily understood from the foregoing descriptions, since the image data have been previously registered in the image data registering unit 7 in order to be utilized when forming the diagnostic report 20, a doctor no longer inputs the desirable image data every time the medical diagnostic report 20 is formed.

Also, it should be noted since the auxiliary memory 11 requires only small memory capacity, a so-called "hard disk memory unit" may be employed instead of the above described floppy disk apparatus 152.

ARRANGEMENT OF SECOND MEDICAL DIAGNOSTIC REPORT FORMING APPARATUS

Figure 5:
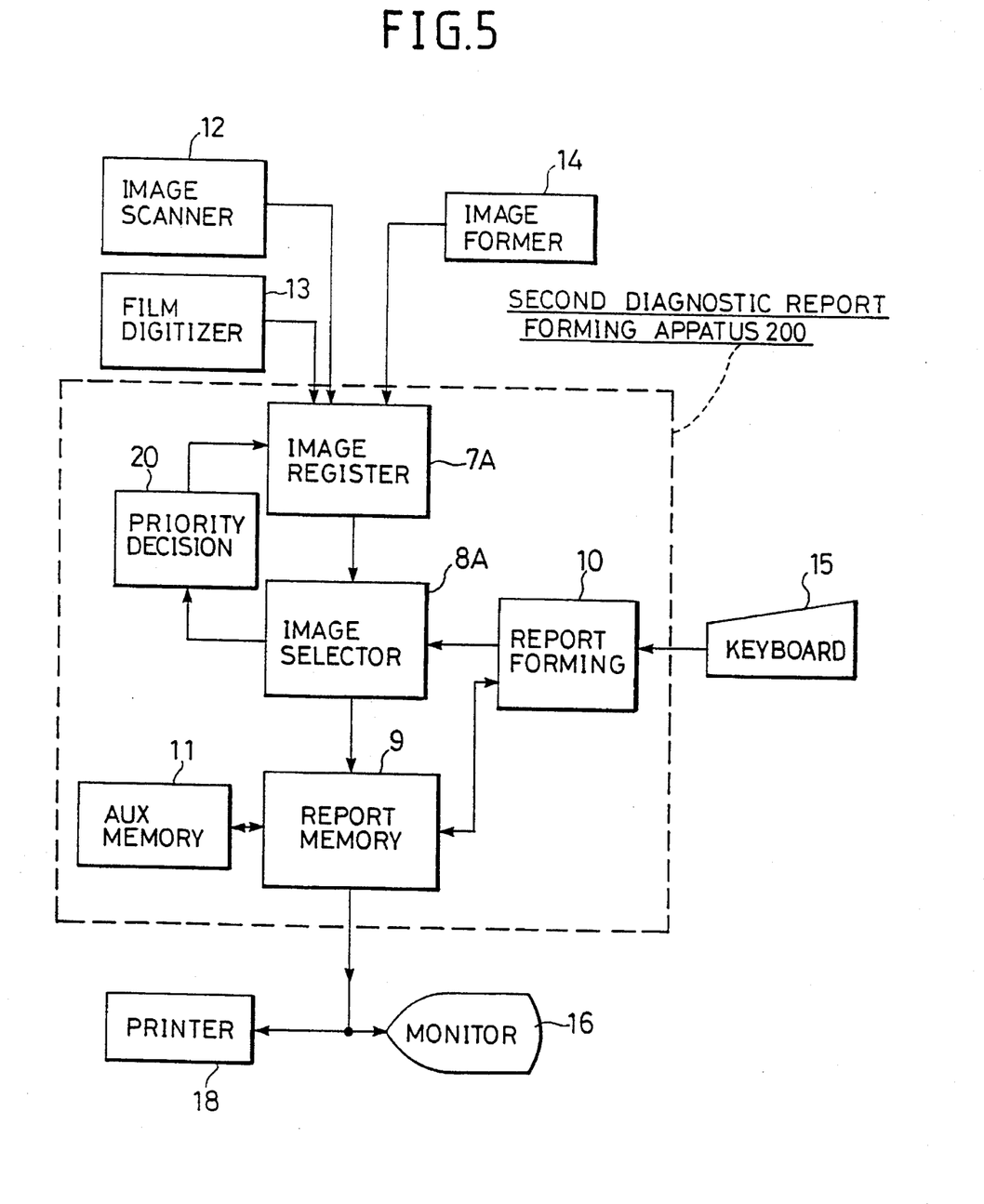
FIG. 5 is a schematic block diagram for showing an overall arrangement of another medical diagnostic report forming apparatus 200 according to a second preferred embodiment of the present invention.

FIG. 5 is a schematic block diagram for showing an overall arrangement of a medical diagnostic report forming apparatus 200 according to a second preferred embodiment of the present invention.

It should be noted that the same reference numerals shown in FIG. 1 will be employed as those for denoting the same or similar circuit elements in the following figures.

As apparent from FIGS. 1 and 5, a major arrangement of the second medical diagnostic report forming apparatus 200 is very similar to that of the first medical diagnostic report forming apparatus 100. Therefore, only different arrangements of the second medical diagnostic report forming apparatus 200 will now be explained.

When various medical image data are acquired from, for example, the image scanner 12, these medical image data are registered into an image data registering unit 7A with having preselected display-priority order, for instance, a serial number. As a consequence, in response to an image-data selecting instruction, these image data registered in the image data registering unit 7A are sequentially selected and derived therefrom by an image data selecting unit 8A. The selected image data is supplied to the medical diagnostic report forming memory 9 and also to a display-priority determining unit 20.

Figure 6:
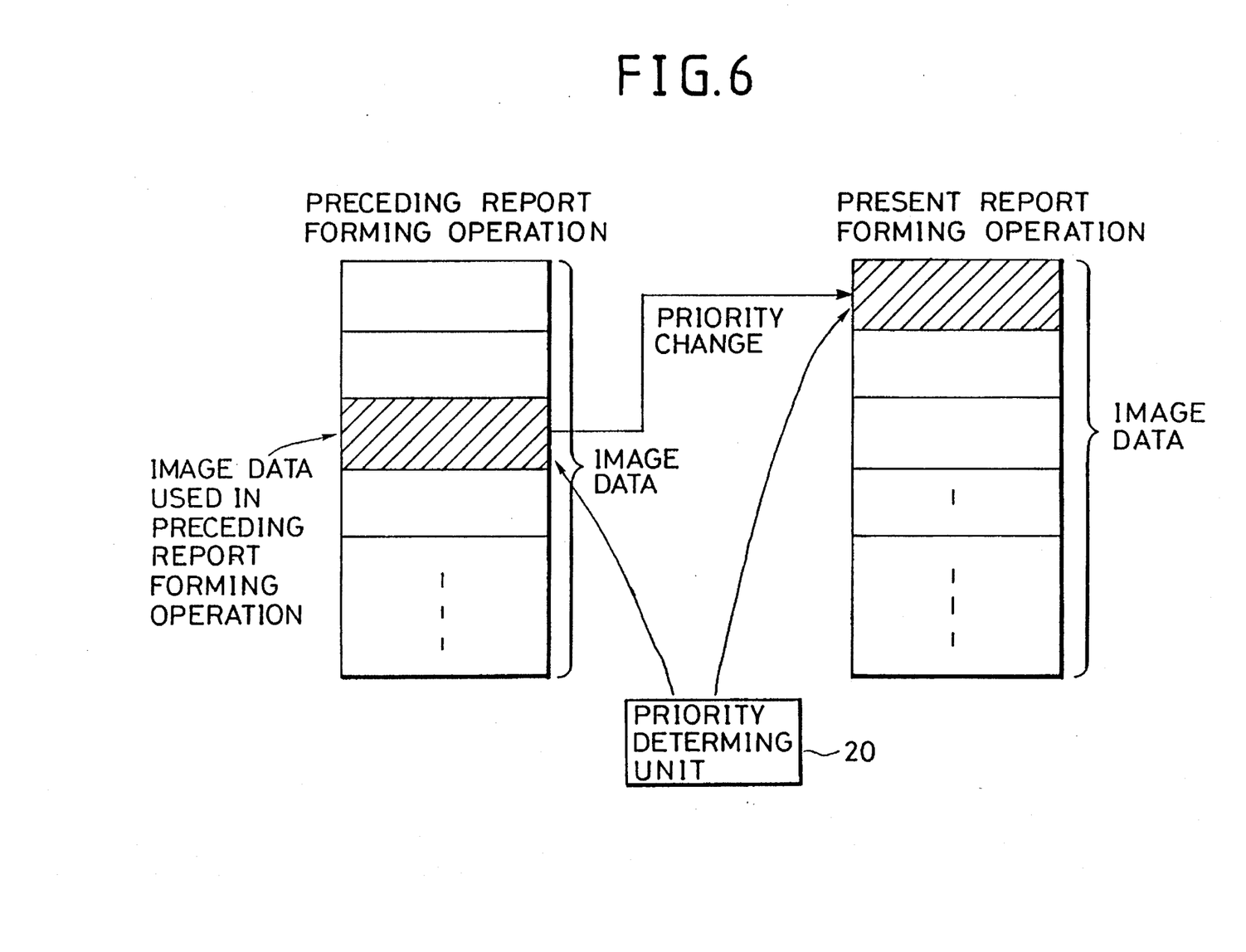
FIG. 6 illustrates how to determine display priority order of the medical image data by the second medical diagnostic report forming apparatus 200.

In the display-priority determining unit 20, the dislay-priority order of the respective image data registered in the image data registering unit 7 is determined, or rearranged. That is, as pictorically explained with reference to FIG. 6, a display-priority decision is established in such a manner that image data selected by the image data selecting unit 8A during a preceding report forming operation has top priority for present report forming operation (will be discussed later).

Furthermore, a printer 18 is connected to the report forming memory 9.

DISPLAY-PRIORITY DETERMINING OPERATION

It should be noted that since both the overall operation of the second medical diagnostic report forming apparatus 200 and the display-priority determining operation thereof functioning as the major feature of the second preferred embodiment are realized by such an internal arrangement of the second report forming apparatus 200 very similar to that of the first report forming apparatus 100, no further drawing is made in the specification, but only a specialized flow operation will now be explained.

Figure 7A:
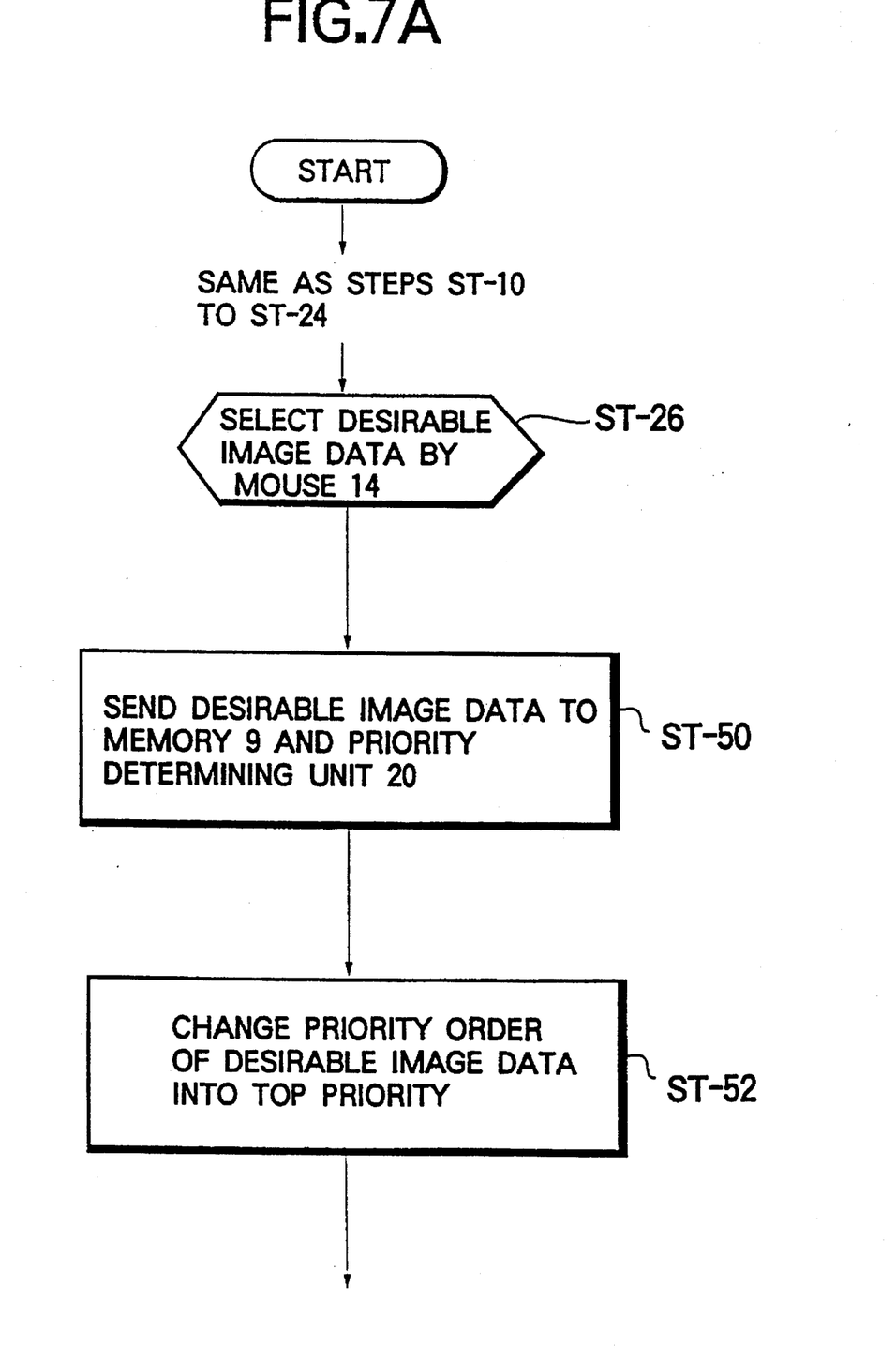
FIG. 7 is a flow chart for explaining the decision on the display priority order of the medical image data performed in the second medical diagnostic report forming apparatus 200.
Figure 7B:
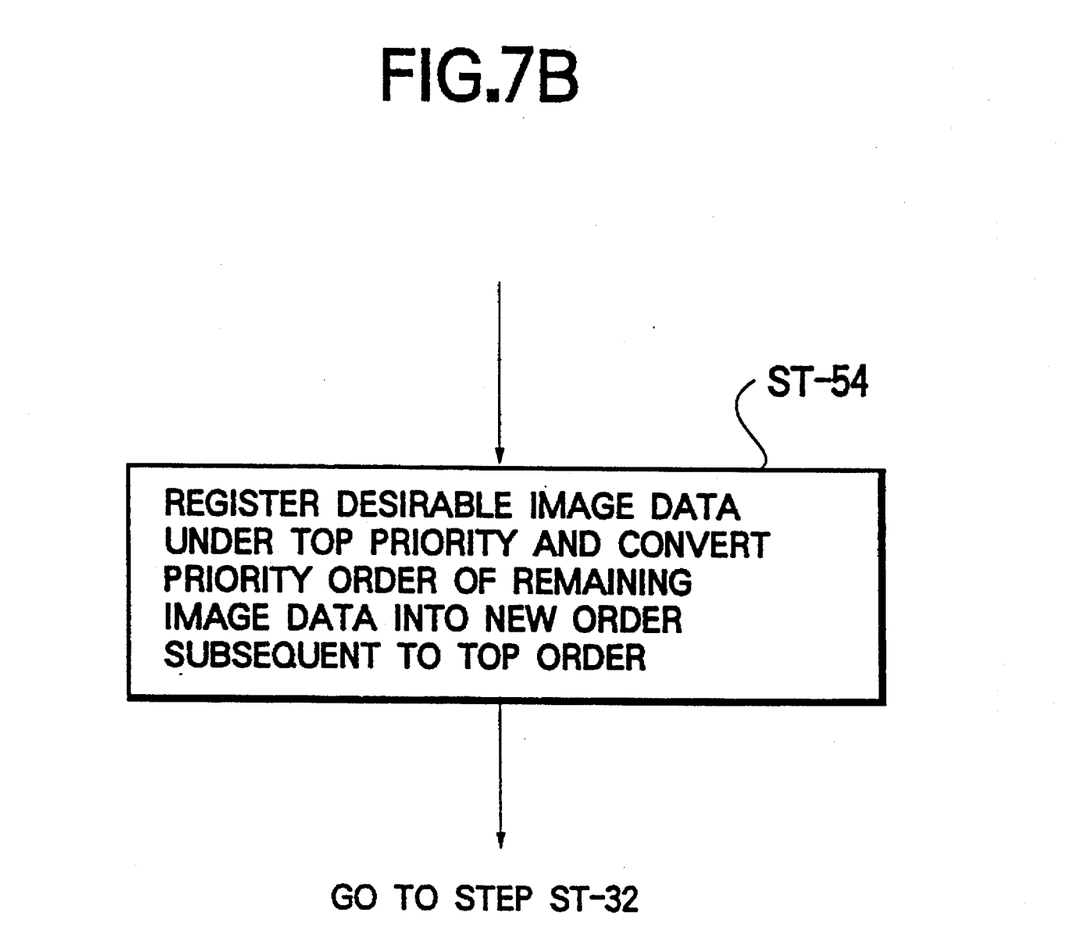

FIG. 7 is a flow chart for explaining such a specialized flow operation, namely display-priority order decision performed by the display-priority determining unit 20.

Since the flow operations as defined from the steps ST-10 to ST-24 of the first diagnostic report forming apparatus 100 are similarly executed in the second diagnostic report forming apparatus 200, no further explanations thereof are made.

In summary, it is assumed that all of the image data acquired from these image scanner 12 and film digitizer 13 have been previously registered with having predetermined display-priority order, for instance, serial numbers. For instance, the first registered image data owns first display-priority order.

Figure 8:
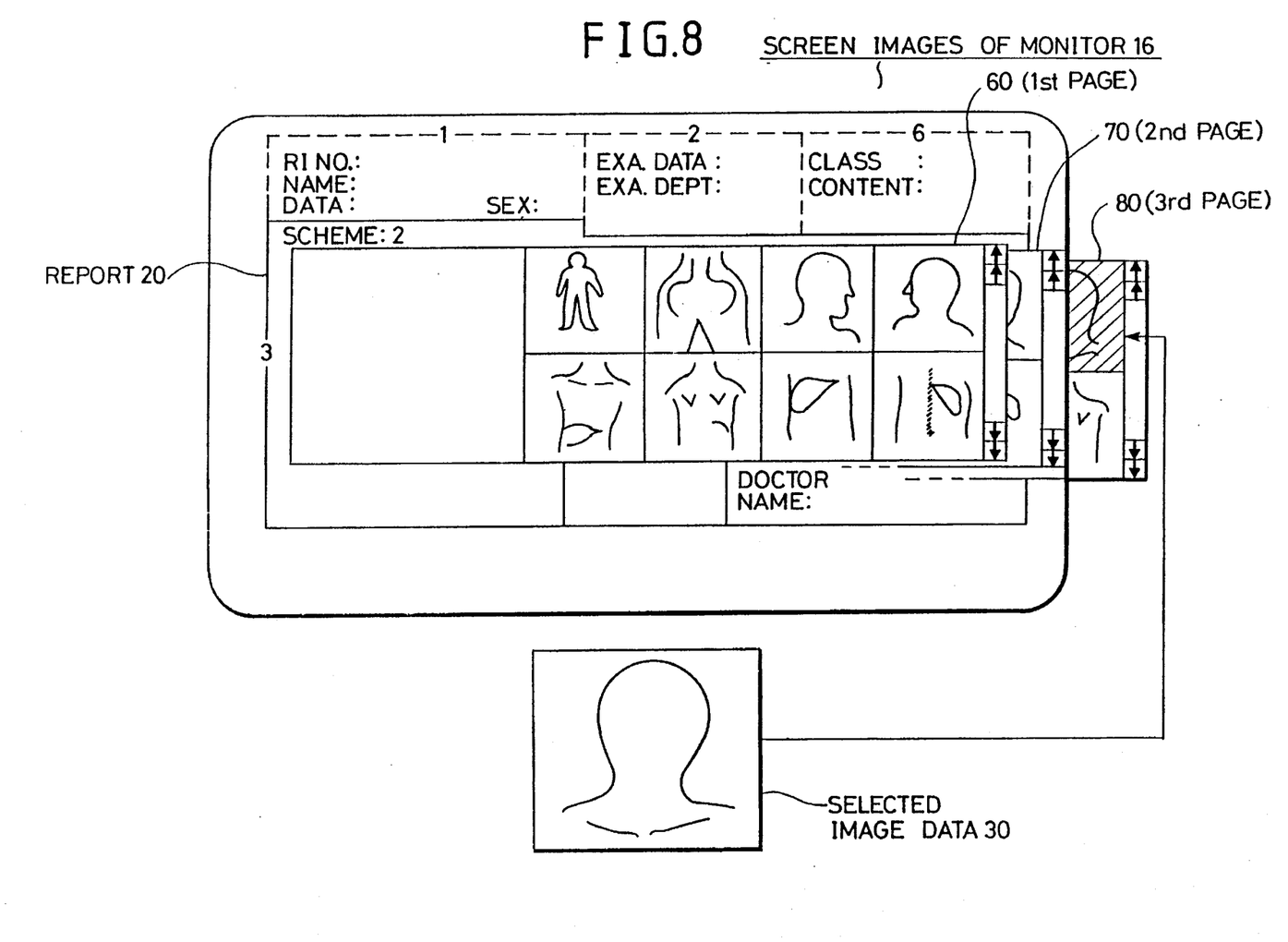
FIGS. 8 and 9 represent how to seek a desirable image displayed on the monitor, according to the second medical diagnostic report forming apparatus 200.

Since the diagnostic report forming unit 10 furnishes the image selecting instruction to the image selecting unit 8A, all of the image data registered in the image data registering unit 7A are successively read in the order of higher display-priority, and successively displayed on the monitor 16. As a result, as shown in FIG. 8, for example, a first page 60 containing 8 sheets of image data having the higher display-priority order is displayed. Then, a doctor starts to seek the desirable image data from 8 sheets of image data. If no desirable image data is found out, then a second page 70 containing 8 sheets of image data is displayed, which are different from the above-described image data of the first page 60. If no desirable image data is seeked, then a third page 80 is displayed. When the desirable image data 30 having preselected display-priority order can be founded out at the third page 80, the doctor selects this image data 30 by manipulating the mouse 14 at the step ST-26 of FIG. 7.

At a next step ST-50, the selected image data 30 is supplied to not only the report forming memory 9, but also the display-priority determining unit 20. In the display-priority determining unit 20, the above-defined display-priority order of the selected image data 30 is changed into a top priority, namely first priority order, at a step 52. Subsequently, the selected image data 30 having the top priority is sent back to the image data registering unit 7A so as to be reregistered therein, and also all of the display-priority order of the remaining image data previously registered therein are converted or rearranged into new priority order, taking account of this top priority by utilizing a priority order conversion table (not shown in detail) stored in the main memory 140 at a step-54.

Figures 4, 4A:
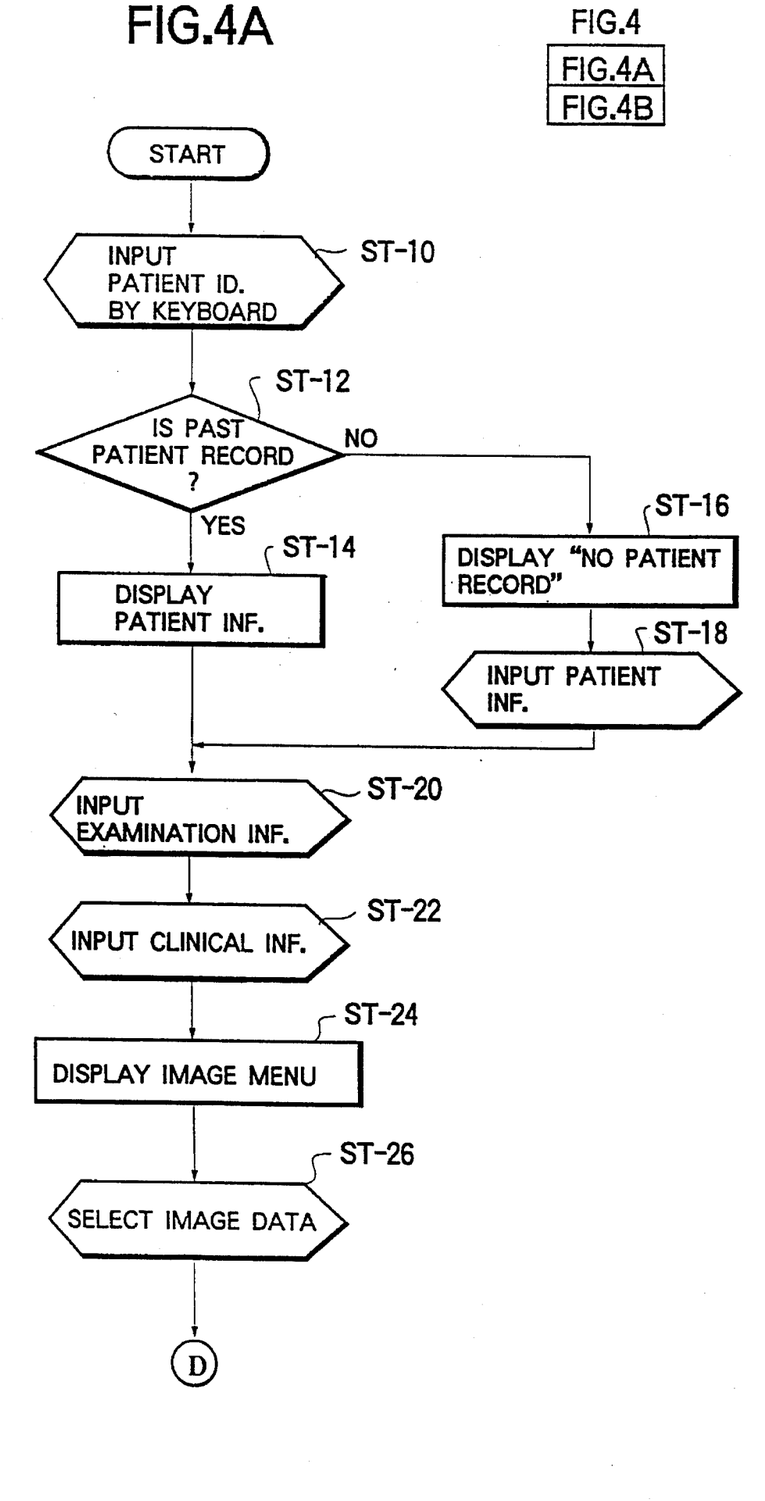
FIG. 4 is a flow chart for explaining a medical diagnostic report forming operation performed in the first report forming apparatus 100.
Figure 4B:
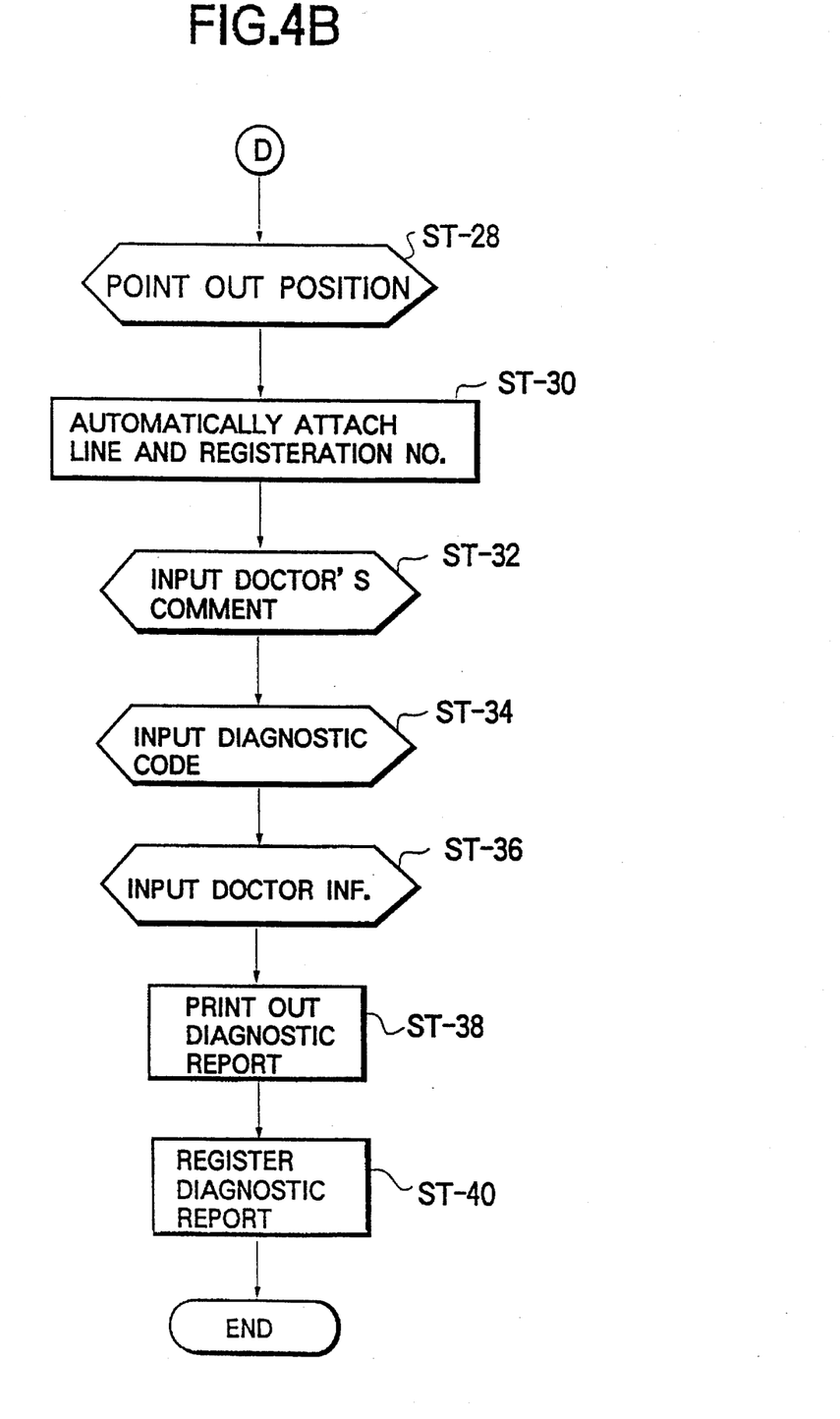

Thereafter, the report forming process is advanced to the step ST-32 shown in FIG. 4 at which the doctor's comment information is written in the column 3 of the diagnostic report 20. Then, other necessary information and code are additionally written in the diagnostic report 20 formed in the report forming memory 9 and the resultant first diagnostic report 20 is stored in the auxiliary memory 11. Accordingly, the first report forming operation is accomplished.

Figure 9:
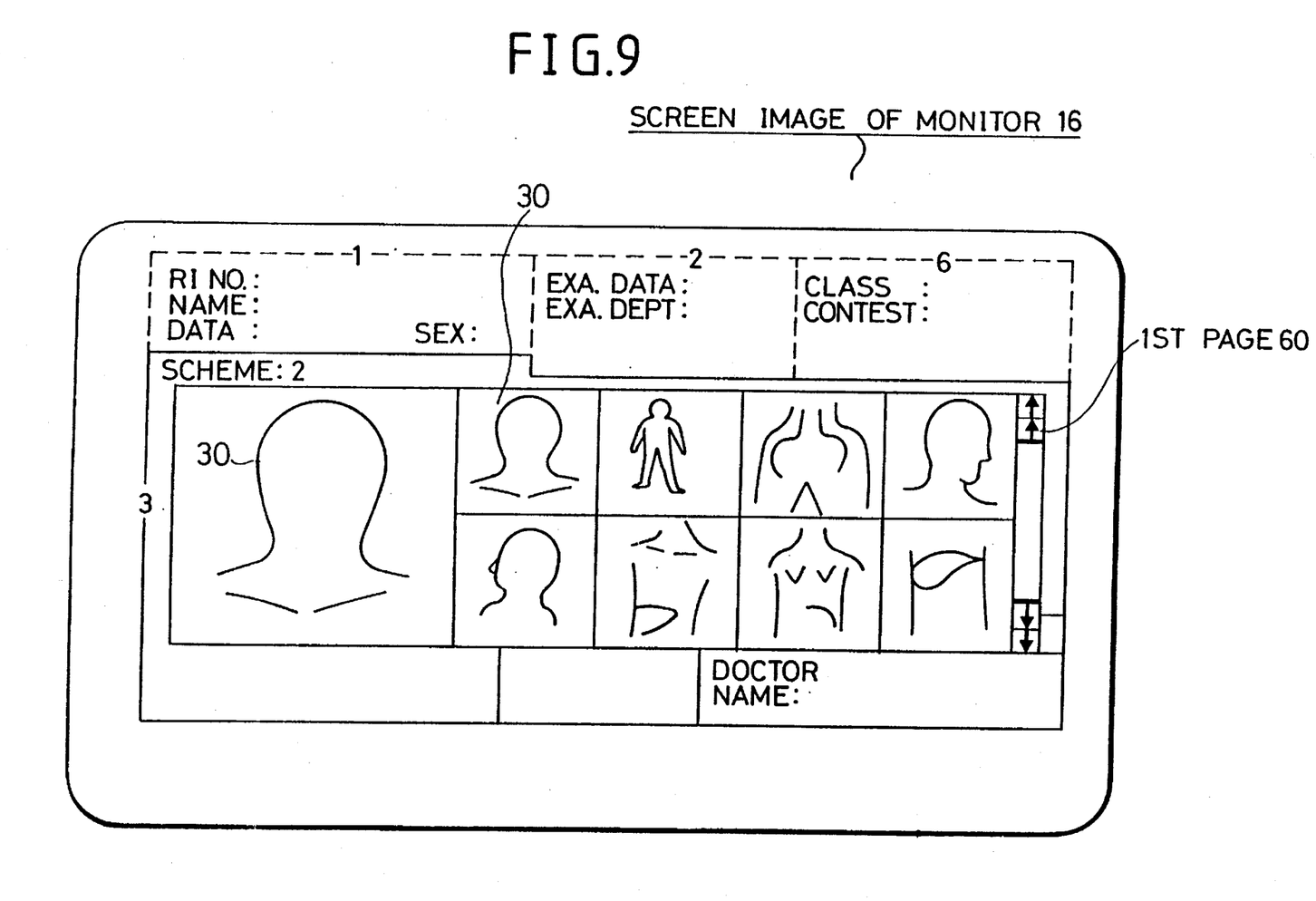

When a second diagnostic report forming operation is carried out, the above-described image data 30 appears at the first image position of the first page 60 as shown in FIG. 9 on the screen of the monitor 16. In other words, the image data which has been selected and used to form the diagnostic report 20 during the previous or preceding report forming operation, is displayed at top priority during the present report forming operation.

As a consequence, there is such a particular advantage that since the images having the higher display-priority order registered in the registering unit 7A are always displayed on the monitor 16 at first, any doctors can readily and quickly retrieve the desirable image data from a large quantity of image data registered therein. In other words, according to the merit of the second diagnostic report forming apparatus 20, as the images having the rather high selection-priority are firstly listed up on the monitor 16, every doctor can easily and quickly retrieve the desirable images, whereby the workloads of forming the diagnostic reports given to the doctors can be considerably lowered.

What is claimed is:

1. A medical diagnostic report forming apparatus for generating a medical diagnosis report regarding a patient's clinical image by a medical doctor's manipulation, the apparatus comprising:

image data registering means for previously registering therein a plurality of medical diagnostic image data representative of typical diagnosis images which are not derived from the patient's clinical image, with registration numbers being attached to said plurality of medical diagnostic image data;

means for extracting preselected medical diagnostic image data having a resemblance close to the patient's clinical image from said plurality of medical diagnostic image data registered in said image data registering means;

means for entering comment data from the doctor related to said preselected diagnostic image data;

first memory means into which both of said preselected medical diagnostic image data and said doctor's comment data are written and electronically combined with each other, thereby forming medical diagnostic report data;

second memory means into which said medical diagnostic report data is stored, said preselected medical diagnostic image data being stored in a form of said registration number; and display means accessible to said second memory means by way of said first memory means, for displaying a content of said medical diagnostic report data stored in said second memory means by retrieving said doctor's comment data and said preselected medical diagnostic image data from said image data registering means based upon said registration number attached thereto, and wherein upon retrieval of said medical diagnostic report data from said second memory means, said first memory means is supplied with said medical diagnostic report data from said second memory means, and said first memory means combines said preselected medical diagnostic image data from said image data registering means based upon said registration number with said doctor's comment data such that said display means displays said preselected medical diagnostic image data and said doctor's comment data.

2. A medical diagnostic report forming apparatus as claimed in claim 1, wherein said second memory means includes a hard disk memory device.

3. A medical diagnostic report forming apparatus as claimed in claim 1, wherein said second memory means includes a floppy disk memory device.

4. A medical diagnostic report forming apparatus as claimed in claim 1, wherein said image data extracting means includes an interactive module to extract said preselected diagnostic image data in an interactive mode.

5. A medical diagnostic report forming apparatus as claimed in claim 1, further including one of an image scanner, a film digitizer and a mouse in communication with said image data and wherein said image data registering means registers said plurality of medical diagnostic image data on the patients acquired by said one of an image scanner, a film digitizer and a mouse.

6. A medical diagnostic report forming apparatus as claimed in claim 1, wherein said means for entering the doctor's comment data is a keyboard.

7. A medical diagnostic report forming apparatus comprising:

image data registering means for previously registering therein a plurality of medical diagnostic image data on patients with registration numbers being attached to said plurality of medical diagnostic image data;

means for extracting preselected medical diagnostic image data from said plurality of medical diagnostic image data registered in said image data registering means;

means for entering doctor's comments data related to said preselected diagnostic image data;

first memory means into which both of said preselected medical diagnostic image data and said doctor's comment data are written and electronically combined with each other, thereby forming medical diagnostic report data;

second memory means into which said medical diagnostic report data is stored, said preselected medical diagnostic image data being stored in a form of said registration number;

means for rearranging said registration numbers of said plurality of medical diagnostic image data based upon preselected diagnostic image data selected in a preceding report forming operation occurring prior to rearranging by said means for rearranging such that said preselected diagnostic image data selected in said preceding report forming operation has top priority to be extracted first by said image data extracting means during a subsequent report forming operation; and display means accessible to said second memory means, for displaying a content of said medical diagnostic image data stored in said second memory means by retrieving said doctor's comment data and said preselected medical image data from said image data registering means based upon said registration number attached thereto.

8. A medical diagnostic report forming apparatus as claimed in claim 7, wherein said registration number rearranging means includes a priority-order conversion table for converting said registration numbers of the medical diagnostic image data into different registration numbers.

9. A medical diagnostic report forming apparatus as claimed in claim 7, wherein said second memory means includes a hard disk memory device.

10. A medical diagnostic report forming apparatus as claimed in claim 7, wherein said second memory means includes a floppy disk memory device.

11. A medical diagnostic report forming apparatus as claimed in claim 7, wherein said image data extracting means includes an interactive module to extract said preselected diagnostic image data in an interactive mode.

12. A medical diagnostic report forming apparatus as claimed in claim 7, further including one of an image scanner, a film digitizer and a mouse in communication with said image registering means and wherein said image registering means registers said plurality of medical diagnostic image data on the patients, acquired by said one of an image scanner, a film digitizer and a mouse.

13. A medical diagnostic report forming apparatus as claimed in claim 7, wherein said means for entering the doctor's comment data is a keyboard.

\* \* \* \* \*

UNITED STATES PATENT AND TRADEMARK OFFICE
CERTIFICATE OF CORRECTION

PATENT NO. : 5,581,460
DATED : December 3, 1996
INVENTOR(S) : TAKASHI KOTAKE ET AL It is certified that error appears in the above-identified patent and that said Letters Patent is hereby corrected as shown below:

In column 3, line 46, change "Overalll" to
--Overall--.
    In column 6, line 11, change "120." to --120--;
        line 47, change "menue" to --menu--.
    In column 8, line 23, change "seeked" to --sought--;
        line 64, change "firstly" to --first--.

Signed and Sealed this

Twenty-eighth Day of October, 1997

Attest:

BRUCE LEHMAN

Attesting Officer    Commissioner of Patents and Trademarks